United States Patent [19]

Perri

[11] 4,182,341

[45] Jan. 8, 1980

[54] EYED NEEDLE CONVERTED FROM A DRILLED END OR CHANNEL END NEEDLE

[75] Inventor: Santo Perri, Danbury, Conn.

[73] Assignee: American Cyanamid Company, Stamford, Conn.

[21] Appl. No.: 839,689

[22] Filed: Oct. 5, 1977

[51] Int. Cl.[2] .............................................. A61B 17/06
[52] U.S. Cl. .................................... 128/339; 223/102
[58] Field of Search ..................... 128/335.5, 339, 340; 223/102

[56] References Cited

U.S. PATENT DOCUMENTS

| | | | |
|---|---|---|---|
| 1,293,660 | 2/1919 | Armstrong | 223/102 |
| 1,960,117 | 5/1934 | Lydreard | 128/339 |
| 2,716,515 | 8/1955 | Moghadam | 223/102 |
| 3,534,740 | 10/1970 | Thompson | 128/339 |
| 3,762,418 | 10/1973 | Wasson | 128/339 |

*Primary Examiner*—Dalton L. Truluck
*Attorney, Agent, or Firm*—Charles F. Costello, Jr.

[57] ABSTRACT

An eyed needle is described which comprises a pointed end and a butt end, a hole or channel bored into the butt end along the length of the needle, a flexible polymer strand formed into a loop, the ends of the loop placed into the hole or channel, and means of securing the ends of the loop in the needle.

8 Claims, 4 Drawing Figures

EYED NEEDLE CONVERTED FROM A DRILLED END OR CHANNEL END NEEDLE

BACKGROUND OF THE INVENTION

This invention relates to a drilled end or channel end needle converted into an eyed needle by attaching a loop formed from a flexible polymer strand to the drilled end or channel end needle. This invention also relates to a method for using the eyed needle as a surgical needle-suture combination.

Surgical needles, regardless of type or purpose, usually take one of three forms: drilled end, that is with a hole bored down the long axis of the needle and a suture positioned in the bore and crimped so that the suture is firmly attached to the needle; or open end (or channeled); or "eyed", that is, stamped, in the manner of a common sewing needle, with no suture attached so that the doctor can thread a suture of his choice.

The problem involved in threading a suture material through the fine eye of a surgical needle is obvious. This invention is useful in providing a large oval diameter threading target which will flex back to an oval diameter configuration for rethreading after use.

Applicant is not aware of any prior art references which in his judgment as one skilled in the surgical needle art, would anticipate or render obvious the eyed needle of the instant invention. For the purpose of fully developing the background of the invention, however, and establishing the state of the requisite art, the following references are set forth: U.S. Pat. No. 2,716,515 which discloses a fast-threading eyed needle and U.S. Pat. No. 1,960,117 which discloses sutures useful with a self-threading or spring eyed needle. These patents are incorporated herein by reference.

This invention has advantages over these prior art patents. The eyed needle is converted from a drilled end or channel end needle. Therefore, conventional machinery can be used. Because a polymer strand is used, the loop will compress during tissue passage but will flex back to an oval diameter configuration for threading. Thus, a large threading target is maintained.

Finally, the double thickness of the surgical suture and the double thickness of the loop can be reduced to just the thickness of the non-crimped needle diameter. In this regard, the needle and the loop are Atraumatic ®, Davis & Geck Co., Danbury, Ct., during passage through living tissue. This is, of course, dependent on the size of the needle, the suture and the loop.

This invention describes a method of using a loop, which can be of surgical suture material, representing a large target for threading, firmly fixed to a drilled end or channel end needle. The eyed needle of this invention is manufactured by attaching a flexible loop of a polymeric material to the drilled end or the channel end of the needle. The loop can be made of any polymeric monofilament material of sufficient flexibility such that the loop will compress during tissue passage but will flex back to an oval diameter configuration for rethreading, e.g., Dermalon ®, DuPont Co., Wilmington, Delaware.

The double ends of the loop are placed in the hole or channel of the needle and then crimped between dies. If a drilled end needle, the double thickness of the loop is less than the thickness of the drilled hole. The loop is forced into a thin oval during passage through tissue.

SUMMARY OF THE INVENTION

The most common type of surgical needle is a single use needle of appropriate size and shape which is crimped to the end of the suture, so that the needle is used but once and then discarded. The attachment can be either a "drilled end" needle, that is, one in which a concentric hole is formed in the end of the needle in which the suture is placed and the needle crimped around the suture; or a "flange" needle in which a U-shaped channel is stamped into the end of the needle with the ends of the U being crimped about the suture to hold the suture. The present invention converts this drilled end or channel end needle into an eyed needle.

The eyed needle of the present invention converted from a drilled end or channel end needle comprises a pointed end and a butt end in which a hole or channel is bored into the butt end along the length of the needle. To convert the needle into an eyed needle, a loop of a flexible polymer strand is formed and the ends of the loop are placed into the hole or channel. The ends of the loop are secured in the hole or channel by any adequate means, e.g., by crimping or by an adhesive. In the preferred embodiment, the means for securing the ends of the loop is by crimping. The eyed needle of the present invention presents a large threading target.

In the preferred embodiment, the eyed needle of the present invention is a surgical needle. In the most preferred embodiment, the eyed needle is a surgical needle selected from the group consisting of pointed straight, pointed curved, three cornered straight, three cornered curved, reverse cutting straight, reverse cutting curved, side cutting straight and side cutting curved.

Also in the preferred embodiment, the flexible polymer strand formed into a loop is a surgical suture strand. In the most preferred embodiment, the surgical suture strand formed into a loop is selected from the group consisting of nylon, polyester, polyethylene and polypropylene. It is to be understood that the flexibility of the surgical suture strand formed into a loop is dependent on the size of the loop and the diameter and type of the fiber used. As a general statement, any loop size and diameter can be used as long as the elastic limit and the loop holding strength of the polymer strand is not exceeded. The flexible polymer strand formed into a loop from a monofilament surgical suture strand of Dermalon ®, DuPont Co., Wilmington, Delaware., is within the scope of the most preferred embodiment. Alternatively, the surgical suture strand formed into a loop is selected from the group consisting of catgut, collagen or polyglycolic acid. It is to be understood that these polymer strands are bioabsorbable. Besides being dependent on the size of the loop and the diameter and type of fiber used, described above, therefore, the modulus of elasticity, the loop holding strength and the elastic limit of these polymer strands will be lowered with repeated use in living tissue.

Also within the scope of the present invention is the method of using the eyed needle disclosed above in suturing. The method comprises inserting by hand or by a threading instrument a surgical suture strand through the flexible polymer strand formed into a loop such that a needle-suture combination is formed and then suturing tissue with the needle-suture combination.

In the preferred embodiment, the surgical needle used in the method is selected from the group consisting of pointed straight, pointed curved, three cornered straight, three cornered curved, reverse cutting straight, reverse cutting curved, side cutting straight and side cutting curved.

Also in the preferred embodiment, the surgical suture strand used in the method is selected from the group consisting of silk, cotton, nylon, polyester, polyethylene. polypropylene and steel.

Alternatively, the surgical suture strand is selected from the group consisting of catgut, collagen or polyglycolic acid.

DETAILED DESCRIPTION OF THE DRAWINGS

FIG. 1 is a side view of a loop placed into the hole of a drilled end needle.

FIG. 2 describes FIG. 1 after crimping, showing the reduction in the minor diameter of the loop oval.

DESCRIPTION OF THE PREFERRED EMBODIMENT

Figure 1:
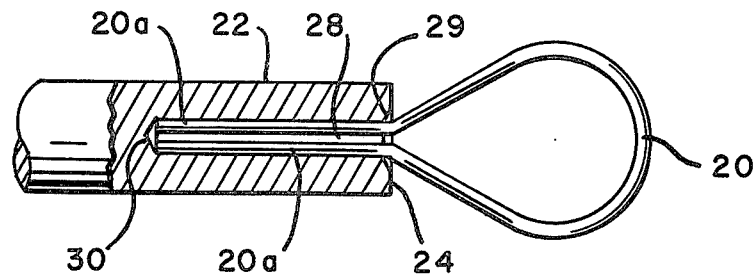
Figure 2:
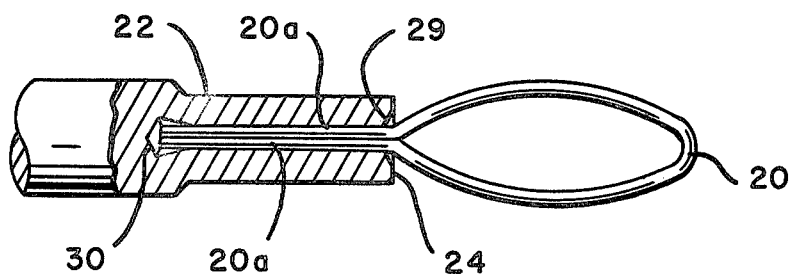

In FIG. 1, the blunt end 24 of the needle 22 has therein a drilled hole 28. In the trade, the hole is referred to as a drilled hole even though it may have been made by the use of a laser beam or other technique. As shown in FIGS. 1 and 2 a slight contersink 29 prevents a sharp corner being present at the exit from the drilled hole and aids in placing the loop 20 and more specifically, the ends of the loop 20a into the drilled hole. The bottom end of the drilled hole may have a conventional slightly conical shape, here called a drill point 30.

In FIG. 2, after the ends of the loop are placed into the drill hole, the blunt end of the needle is crimped about the ends of the loop 20a. Although a crimp along almost the entire length of the drilled hole 28 (see FIG. 1) is described in FIG. 2, it is to be understood that the needle can be crimped about the ends of the loop 20a anywhere along the length of the drilled hole 28 as long as the loop is held with sufficient force to the needle.

The crimping can be accomplished with swaging dies. The swaging dies preferably are of an extremely hard material such as tungsten carbide. The dies are symmetrical and conveniently have a rectangular cross section, which slide in ways. The ways are conventional and provide for moving the swaging dies equally towards each other without lost motion. The crimping method used to secure the ends of the loop formed from the flexible polymer strand is not important as long as the loop is held with sufficient force to the needle.

In FIG. 2, the drilled end 28(described in FIG. 1) is crimped for substantially its full length with a cylindrical crimp about the suture. This is a conventional crimping method for surgical needles. Usually a double closing of dies is required to give such a round crimp. In such conventional crimp, the end of the suture is held by friction only and because of manufacturing variations, must be held tightly to insure that the needle attachment is adequate.

In production, it is customary to set the closing crimp of the dies by measuring individual test eyed needles to give values well within production limits, so that manufacturing tolerances in needle diameter, hole inside diameter, flexible polymer strand size, and crimp itself, on a single swaging machine, permit production within acceptable limits. Each swaging machine is set separately, and tests are made periodically to be sure the loop is held with sufficient force to the needle.

Figure 3:
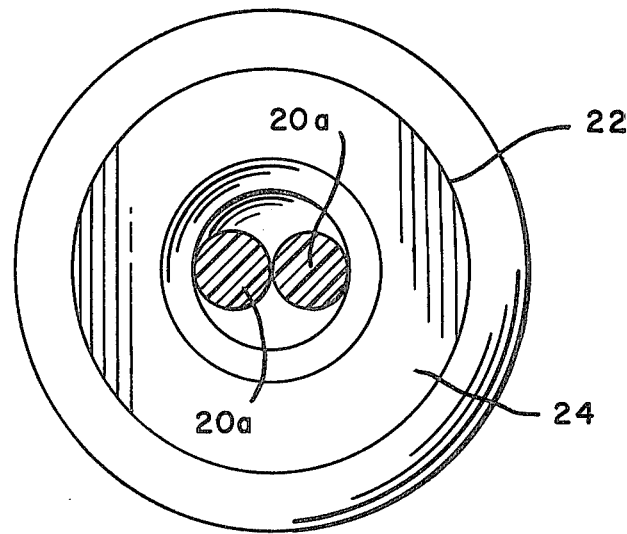
FIG. 3 is a bottom view of FIG. 2 showing the crimped cross-sectional area of the loop and drilled end needle.

FIG. 3 is a cross-sectional bottom view of FIG. 2 at the blunt end 24 showing the ends of the loop 20a inside the diameter of the crimped surgical needle 22. This is the preferred embodiment as the surgical needle passes through tissue. The remainder of the flexible polymer strand compresses. Thus, the eyed needle-suture combination of this invention avoids an unduly large surgical needle hole in passing through tissue and provides a desirably smooth exterior so that the needle will slide through the tissue with a minimum of damage.

Figure 4:
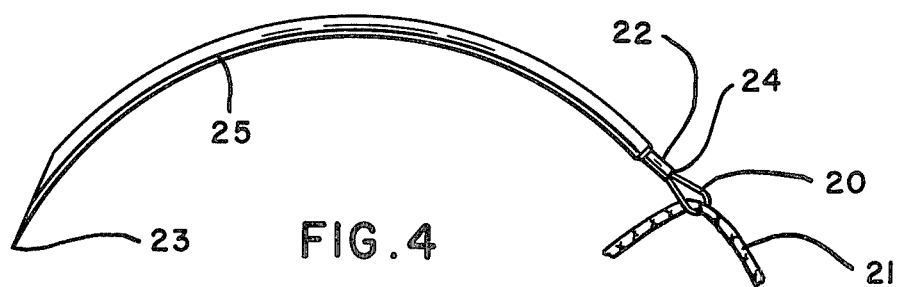
FIG. 4 is a side view of a preferred embodiment of the present invention threaded with a suture strand.

As shown in FIG. 4, a braided surgical suture 21 is threaded to an eyed surgical needle 22. The eyed surgical needle has a penetrating point 23 at the front end and has a loop 20 crimped to the blunt end 24. The surgical needle itself may be of any of the conventional configurations such as straight or curved, and a conical point, a triangular point, cutting or reversed cutting, or a duck bill or spade point to meet with the preference of the user. The shank 25 can be round, slightly flattened, or with ridges or grooves to aid in gripping by needle forceps. When the shank is round, in the preferred embodiment the loop is in the plane of the round shank, as shown in FIG. 4.

Although a braided surgical suture is described in FIG. 4, it is to be understood that the surgical suture can be of any conventional suture material, braided, twisted or monofilament. Typical materials include silk, nylon, linen, cotton, polyethylene, polypropylene, steel and natural materials such as catgut, and synthetic polymers having glycolic acid ester linkages subject to hydrolytic degradation to non-toxic, tissue compatible absorbably components, including polyglycolic acid. It is important that the end of the braided or twisted surgical suture be free from distortion as this aids the threading of the suture into the loop oval. A flattened or multilated cut can so enlarge the end of a suture that it does not thread smoothly into the eyed needle.

The conversion of a drilled end or channel end needle into an eyed needle by this invention can be manufactured to the tolerences prescribed for the attachment of absorbable or nonabsorbable surgical sutures to eyeless needles described in "The United States Pharmacopeia", 19th rev., 7/75, U.S. Pharm. Convention, Inc., Rockville, Md., p. 666 which is incorporated by reference.

I claim:

1. An eyed needle which has a large threading target comprising: a pointed end; a butt end; a hole or channel bored into said butt end along the length of said needle; a loop formed from a flexible polymer strand with the ends of said loop placed into said hole or channel; and attachment means for securing said ends in said hole or channel.

2. An eyed needle of claim 1 wherein the needle is a surgical needle.

3. An eyed needle of claim 2 wherein the flexiable polymer strand is selected from the group consisting of nylon, polyester, polyethylene and polypropylene.

4. An eyed needle of claim 2 wherein the flexiable polymer strand is selected from the group consisting of catgut, collagen and polyglycolic acid.

5. An eyed needle of claim 1 wherein the attachment means for securing said ends is a crimp.

6. The method of using the eyed needle of claim 2 in suturing which comprises inserting by hand or by a threading instrument a surgical suture strand through said loop such that a needle-suture combination is formed and suturing tissue with said needle-suture combination.

7. The method of claim 6 wherein the surgical suture strand is selected from the group consisting of silk, cotton, nylon, polyester, polyethylene, polypropylene, and steel.

8. The method of claim 6 wherein the surgical suture strand is selected from the group consisting of catgut, collagen and polyglycolic acid.

* * * * *